(12) United States Patent
Amary et al.

(10) Patent No.: US 8,310,675 B2
(45) Date of Patent: Nov. 13, 2012

(54) SYSTEM AND PROCESS FOR ANALYZING A SAMPLE

(75) Inventors: Pascal Amary, Orleans (FR); Ramdane Benferhat, Oncy sur Ecole (FR); Denis Cattelan, Antony (FR)

(73) Assignee: Horiba Jobin Yvon SAS (FR)

( * ) Notice: Subject to any disclaimer, the term of this patent is extended or adjusted under 35 U.S.C. 154(b) by 469 days.

(21) Appl. No.: 12/523,417

(22) PCT Filed: Jan. 18, 2008

(86) PCT No.: PCT/EP2008/050596
§ 371 (c)(1),
(2), (4) Date: Jan. 18, 2010

(87) PCT Pub. No.: WO2008/087217
PCT Pub. Date: Jul. 24, 2008

(65) Prior Publication Data
US 2010/0110427 A1    May 6, 2010

(30) Foreign Application Priority Data

Jan. 19, 2007  (EP) .................................... 07300736

(51) Int. Cl.
*G01J 4/00* (2006.01)
(52) U.S. Cl. .................................................. 356/369
(58) Field of Classification Search .......... 356/364–369, 356/630
See application file for complete search history.

(56) References Cited

U.S. PATENT DOCUMENTS

| | | | |
|---|---|---|---|
| 5,333,052 A | 7/1994 | Finarov | |
| 5,764,365 A * | 6/1998 | Finarov | 356/630 |
| 6,798,511 B1 | 9/2004 | Zhan et al. | |
| 7,095,498 B2 * | 8/2006 | Horie | 356/364 |
| 2004/0233437 A1 | 11/2004 | Horie | |

FOREIGN PATENT DOCUMENTS

| | | |
|---|---|---|
| EP | 1411333 A1 | 4/2004 |
| WO | 2005083352 A1 | 9/2005 |

* cited by examiner

*Primary Examiner* — Layla Lauchman
(74) *Attorney, Agent, or Firm* — Brooks Kushman P.C.

(57) ABSTRACT

A system and process for analyzing a sample includes an excitation section and an analyze section, said excitation section including a light source emitting an incident measurement luminous beam, a polarization state generator (PSG), first optics, and said analyze section includes a polarization state analyzer (PSA), a detection system and second optics. The excitation section includes an illumination source emitting an incident visualization luminous beam, superposition optics that direct the incident visualization luminous beam toward the sample surface along an optical axis which is identical to the optical axis of the incident measurement luminous beam and the analyze section includes separation optics that transmit a part of the reflected or transmitted visualization luminous beam and a part of the reflected or transmitted measurement luminous beam towards a visualization direction.

21 Claims, 5 Drawing Sheets

SYSTEM AND PROCESS FOR ANALYZING A SAMPLE

The invention concerns a system and a process for analysing a sample such as polarimetric or ellipsometric system.

Polarimetry or ellipsometry are optical techniques that uses polarized light to measure the dielectric properties of a sample. The most common application of polarimetry or ellipsometry is the analysis of very thin films such as layers on wafers.

The use of polarimetry or ellipsometry is particularly attractive. They are nondestructive techniques, such that it is suitable for in situ observation, and they are extremely sensitive.

Through the analysis of the state of polarization of the light that interacts with the sample, polarimetry or ellipsometry can yield information about such films like thickness, morphology, or chemical composition.

The most common polarimeter or ellipsometer configuration is a reflection polarimeter or ellipsometer, although transmission polarimeters or ellipsometers are sometime used.

Such polarimetric or ellipsometric systems are disclosed in the documents EP1411333 and U.S. Pat. No. 5,757,671. The surface of a sample is lit by an incident luminous beam and one or more polarization states of this beam is compared to one or more polarization states of the reflected or transmitted luminous beam.

In most cases, it is needed to visualize the spot of light produced by the incident luminous beam at the sample surface. The spot of the incident luminous beam is positioned at the sample surface to analyse a selected area. With samples having a non homogeneous surface, it is interesting to move the spot for analysing different areas.

Figure 1:
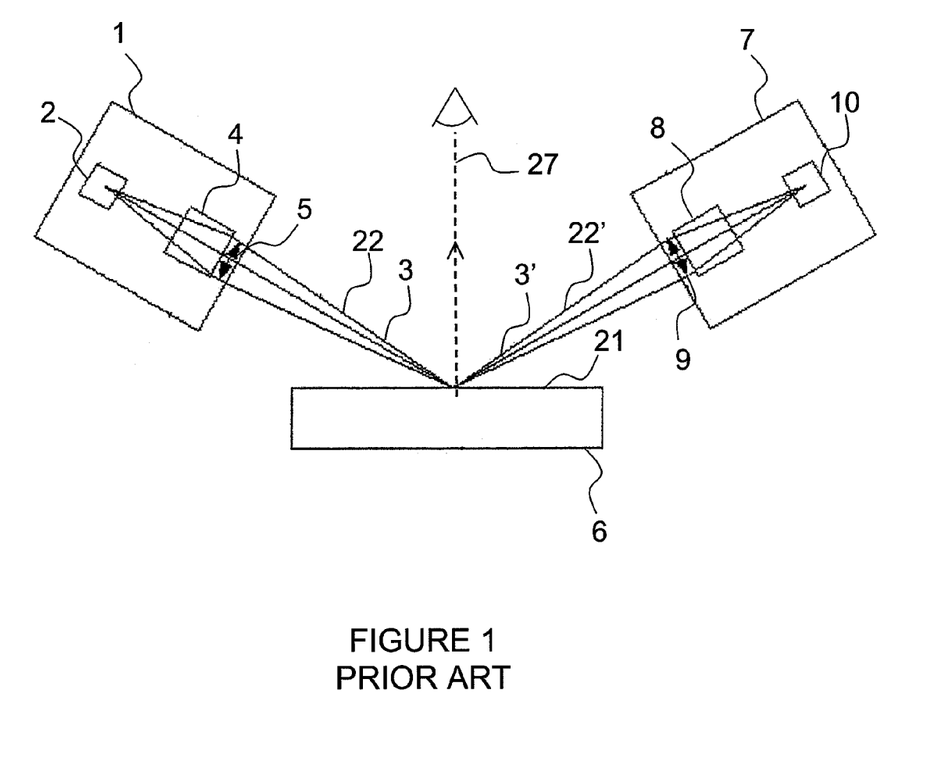
FIG. 1 represents a general configuration of an ellipsometer of the prior art wherein the spot of the incident measurement luminous beam is visualized normally to the sample surface.

The visualization of the spot is usually realised normally to the sample surface, as illustrated on the FIG. 1 of the prior art. This method imposes to use diffusing samples which are capable to diffuse the measurement luminous beam. However, most samples do not diffuse light or diffuse not enough light.

Small size spots (from 10 μm to a few hundred μm) are used for analyzing small areas of samples, and in particular small areas on microscopically patterned samples, such as Integrated Circuits (ICs) or Flat Panel Displays (FPDs). In such applications, it is necessary to precisely position the small spot relatively to the patterned sample surface for proper analysis. But the low intensity of a small spot makes this relative positioning task difficult.

Furthermore, the visualization of the spot of the incident luminous beam at the sample surface or the sample surface is impossible when the measure is realised in enclosed chamber such as electrochemical cell or ablation chamber for example. Such chambers are not provided of transparent porthole disposed over the sample surface.

Document US2004/0233437 discloses a spectroscopic ellipsometer with a lighting part for guiding polarized light to an object, and a light receiving part for receiving reflected light [0015]. The lighting part comprises a light source for ellipsometric measurements, an auxiliary light source and an optical element for superimposing the auxiliary light on light from the light source [0015]. The light receiving part comprises an optical element for extracting the auxiliary light from the reflected light (cf [0015]). According to the embodiment described in this document, the reflected light from the substrate is guided to a cold mirror and only auxiliary light passes through the cold mirror and is extracted [0046]. The extracted auxiliary light forms images of patterns used for focusing and tilt adjustment of the sample [0018] and [0049]. This prior art document does not describe visualization means of an ellipsometer measurement spot and a part of the sample surface around the ellipsometer spot. This document does not describe a spectroscopic ellipsometer combined with an imaging ellipsometer.

One aim of the present invention consists to provide a system for analysing a large variety of samples enabling to visualize the spot of the incident luminous beam on the sample surface and a part of the sample or the whole surface of the sample. With this system, the spot is visualizable on samples which diffuse no light or not enough light. This system is particularly useful to analyse non homogeneous samples.

Another aim of the present invention is to provide a system for analysing a sample enabling to realise simultaneously or successively spectroscopic ellipsometry (or polarimetry) measurements and ellipsometric (or polarimetric) images of a sample.

To this end, the invention concerns a system for analysing a sample having at least a surface and comprising:
an excitation section including:
 a light source able to emit an incident measurement luminous beam,
 a polarisation state generator (PSG) able to receive the incident measurement luminous beam and able to produce one or more independent polarization states of the incident measurement luminous beam,
 first optical means able to focus the incident measurement luminous beam onto the surface of the sample for generating a reflected or transmitted measurement luminous beam having an intensity,
an analyse section comprising:
 a polarisation state analyser (PSA) able to analyse one or more independent polarization states of the reflected or transmitted measurement luminous beam,
 a detection system able to measure intensity of the reflected or transmitted measurement luminous beam as a function of polarization states,
 second optical means able to focus the reflected or transmitted measurement luminous beam onto the detection system.

According to the invention:
the excitation section comprises:
 an illumination source able to emit an incident visualization luminous beam,
 superposition optical means able to send the incident visualization luminous beam in the direction the sample surface along an optical axis which joins the optical axis of the incident measurement luminous beam and to form an enlarged visualization luminous beam spot (40) on the sample surface (21), in order to generate a reflected or transmitted visualization luminous beam, and
the analyse section comprises separation optical means able to transmit a part of the reflected or transmitted visualization luminous beam and a part of the reflected or transmitted measurement luminous beam towards a visualization direction.

According to various embodiments, the present invention also concerns the characteristics below, considered individually or in all their technical possible combinations:
the analyse section comprises an imaging system having a detection surface, said imaging system receiving the part of the reflected visualization luminous beam and the part of the reflected or transmitted measurement luminous beam on the detection surface, the imaging system is an inclined imaging system having a detection surface inclined with respect to the visualization direction according to an inclination angle (α), the light source is a multi-coloured light emitting diode or a wide spectral band light source and the detection system comprises a monochromator or a spectrograph enabling spectroscopic measurement of a measurement spot on the sample surface, the superposition optical means and the separation means comprise rotating mirrors, and the detection system and the imaging system are synchronized with the rotating mirrors for successive spectroscopic measurement of a measurement spot and imaging of an enlarged illuminated area around the measurement spot, the superposition optical means and the separation means comprise elements selected from beamsplitters and beam separating cubes and the detection system and the imaging system are synchronized together for simultaneous spectroscopic measurement of a measurement spot and imaging detection of an enlarged illuminated area around the measurement spot, the light source emitting an incident measurement luminous beam and the illumination source emitting an incident visualization luminous beam are light-emitting diodes, the incident visualization luminous beam emitted by said illumination source having a size superior to the size of the incident measurement luminous beam when projected on the sample surface, the PSG and the PSA comprise liquid crystal (LC) variable retarders, the detection system measuring intensity of the reflected or transmitted measurement luminous beam is a spectrograph, the superposition optical means and the separation optical means are beamsplitters, the first optical means is disposed between the PSG and the sample, the second optical means is disposed between the sample and the PSA, the imaging system is a CCD camera, the imaging system is a hyperspectral detector, said hyperspectral detector receiving a part of the reflected or transmitted visualization luminous beam to produce a spectroscopic image of one sample layer.

Furthermore, the invention concerns a process for analysing a sample comprising the step of realising an ellipsometric measurement at a measurement point on the sample surface.

According to the invention, the process for analysing a sample comprises a step of visualization of an area localized around the measurement point on the sample surface.

According to various embodiments, the present invention also concerns the characteristics below, considered individually or in all their technical possible combinations:

the ellipsometric measurement comprises the operations of:
emission of an incident measurement luminous beam,
production of one or more independent polarization states of the incident measurement luminous beam,
focalisation of the incident measurement luminous beam onto the sample surface for generating a reflected or transmitted measurement luminous beam having an intensity,
analyse of one or more independent polarization states of the reflected or transmitted measurement luminous beam,
measurement of the intensity of the reflected or transmitted measurement luminous beam as a function of polarization states.

the visualization of an area localized around the measurement point on the sample surface comprises the operations of:
emission of an incident visualization luminous beam,
superposition of the incident visualization luminous beam axis with the incident measurement luminous beam axis such that the optical axis of the incident visualization luminous beam joins the optical axis of the incident measurement luminous beam, in order to generate a reflected or transmitted visualization luminous beam, and
transmission of a part of the reflected or transmitted visualization luminous beam and a part of the reflected or transmitted measurement luminous beam towards a visualization direction, the step of visualization of an area localized around the measurement point on the sample surface comprises the operation of detection of the part of the reflected or transmitted visualization luminous beam and the part of the reflected or transmitted measurement luminous beam towards the visualization direction, the step of visualization of an area localized around the measurement point on the sample surface consists of an acquisition of an ellipsometric image of said area on the sample surface.

The description of the invention is illustrated by the following drawings in which.

Said ellipsometer comprises an excitation section 1 and an analyse section 7.

The excitation section 1 comprises a light source 2 emitting an incident measurement luminous beam 3, a polarisation state generator (PSG) 4 and first optical means 5.

The light source 2 can be a laser or a light-emitting diode for monochromatic measurement, or a multicoloured light-emitting diode or a light having a wide spectral band for spectroscopic measurement.

The incident measurement luminous beam 3 passes through the PSG 4 and is focused onto the sample surface 21 through the first optical means 5.

The incident measurement luminous beam 3 is reflected onto the surface 21 producing a reflected measurement luminous beam 3' having an intensity.

The analyse section 7 of the ellipsometer of the prior art comprises a polarisation state analyser (PSA) 8 enabling to analyse one or more independent polarization states of the reflected measurement luminous beam 3', a detection system 10 measuring intensity of the reflected measurement luminous beam 3' as a function of polarization states and second optical means 9.

The reflected measurement luminous beam 3' is send through the second optical means 9 and passes through the PSA 8 before being focused onto the detection system 10.

If the sample 6 diffuses enough the measurement luminous beam 3', a part of the measurement luminous beam 27 is visualized normally to the surface 21. Thus, the spot of light 29 produced by the projection of the incident measurement luminous beam 3 on the sample surface 21 is visualized directly by user eyes or a CCD camera.

However, with such ellipsometer of prior art, the spot of the incident measurement luminous beam 29 is only vizualisable for samples diffusing enough light.

In the case of microscopically patterned samples, the position of a small measurement spot and the sample pattern features are hardly visualizable.

Furthermore, the spot of the incident measurement luminous beam 29 is not vizualisable in apparatus using enclosed chamber.

Figure 2:
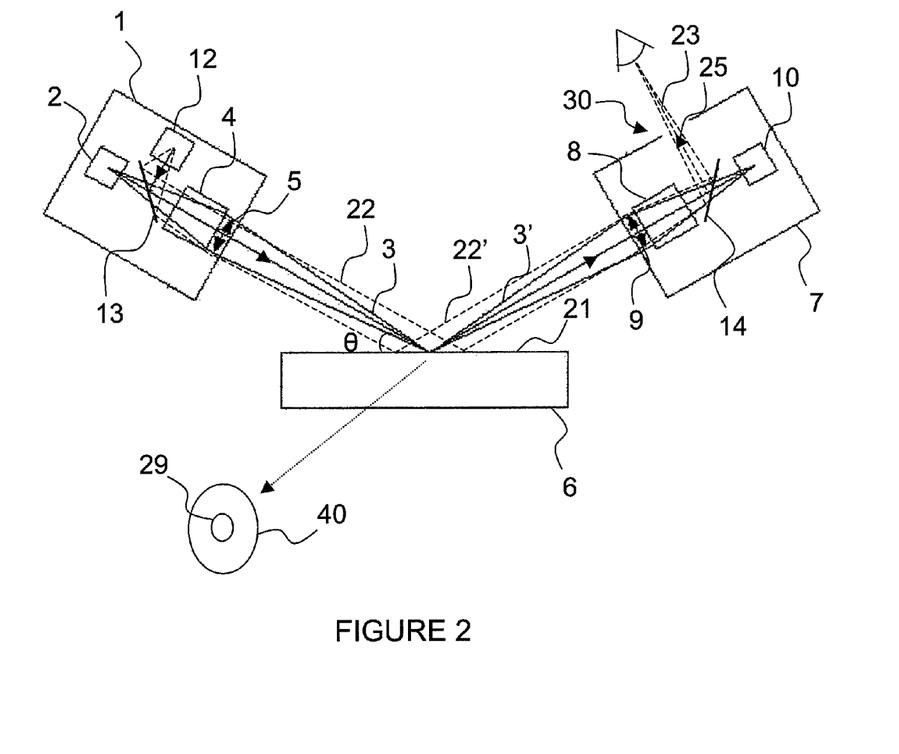
FIG. 2 represents a system for analysing a sample wherein the spot of the incident measurement luminous beam and the sample surface are visualized in the direction of the measure, according to one embodiment of the invention.

FIG. 2 represents a system for analysing a sample wherein the spot of the incident measurement luminous beam 29 and the sample surface 21 are visualized in the direction of the measure, according to one embodiment of the invention.

The system for analysing a sample comprises an excitation section 1 including a light source 2 emitting an incident measurement luminous beam 3, a PSG 4 and first optical means 5.

The excitation section 1 further comprises an illumination source 12 emitting an incident visualization luminous beam 22.

The incident visualization luminous beam 22 is an enlarged luminous beam leading to an enlarged spot of the incident visualization luminous beam 40 on the sample surface 21. Said spot of the incident visualization luminous beam 40 enable to illumine a part of the sample surface 21 or the whole sample surface 21. According to an aspect of the invention, the visualization luminous beam is not focused on the sample surface in order to provide a uniform sample surface illumination.

The method for analysing a sample 6 comprises the step of realising an ellipsometric measurement at a measurement point on the sample surface 21 and a step of visualization of an area localized around the measurement point on the sample surface 21.

The measurement point on the sample surface 21 corresponds to the spot of the incident measurement luminous beam 29. The measurement point on the sample surface 21 have a surface which is smaller than the surface of the area localized around this measurement point.

The area localized around the measurement point on the sample surface 21 corresponds to the spot of the incident visualization luminous beam 40.

The term visualization means a direct observation by user eyes or an indirect visualization on a detector.

The size of the incident visualization luminous beam 22 is greater than the size of the incident measurement luminous beam 3 when projected on the sample surface.

In order to optimize the contrast, the lighting ratio between the incident measurement luminous beam 3 and the incident visualization luminous beam 22 can vary from 10 to 100.

The illumination source 12 can be a light-emitting diode, a multicoloured light-emitting diode or a light having a wide spectral band.

Alternatively, the illumination source 12 can be associated with a holographic diffuser 17 that homogenizes the incident visualization luminous beam 22. The holographique diffuser 17 is disposed between the illumination source 12 and the superposition optical means 13.

The illumination source 12 can be associated with focalisation means for focussing the emitting point of the illumination source 12 on the second optical means 9 in order to realise a Kohler type lighting. The focalisation means is disposed between the illumination source 12 and the superposition optical means 13.

The incident visualization luminous beam 22 is reflected onto a superposition optical means 13 and is directed to the PSG 4.

The superposition optical means 13 can be a beamsplitter or a beam separating cube disposed between the light source 2 and the PSG 4.

The incident visualization luminous beam 22 and the incident measurement luminous beam 3 can be emitted simultaneously or alternatively.

After being polarised by the PSG 4, the incident visualization luminous beam 22 and the incident measurement luminous beam 3 passes through the first optical means 5 which is disposed after the PSG 4 on the FIG. 2.

Alternatively, the first optical means 5 can be disposed before the PSG 4. The first optical means 5 can be lens or the like.

The first optical means 5 can be such that it permits to obtain a spot of light that is limited by the diffraction limit.

The first optical means 5 directs simultaneously or alternatively the incident visualization luminous beam 22 and the incident measurement luminous beam 3 onto the sample surface 21.

The superposition optical means 13 is disposed and configured such that the optical axis of the incident visualization luminous beam 22 is identical to the optical axis of the incident measurement luminous beam 3. Said optical axis comprises the axis between the superposition optical means 13 and the surface 21.

The incident visualization luminous beam 22 and the incident measurement luminous beam 3 make the same incidence angle ($\theta$) with respect to the sample surface 21. In the case of measurements by reflexion, the incidence angle (90-$\theta$) is comprised between 0° and 90° and is advantageously equal to 70°.

The reflexion of the incident measurement luminous beam 3 and the incident visualization luminous beam 22 on the sample surface 21 leads to the generation of a reflected measurement luminous beam 3' and a reflected visualization luminous beam 22', respectively.

The analyse section 7 comprises a detection system 10 and second optical means 9 focusing the reflected measurement luminous beam 3' onto the detection system 10.

The detection system 10 can be a photodiode, a photomultiplier, a monochromator or a spectrograph.

The analyse section 7 comprises a PSA 8 enabling to analyse one or more independent polarization states of the reflected measurement luminous beam 3' and the reflected visualization luminous beam 22'.

The reflected measurement luminous beam 3' passes through the PSA 8 before being detected by the detection system 10.

The analyse section 7 comprises separation optical means 14 enabling to transmit simultaneously or alternatively a part of the reflected visualization luminous beam 23 and a part the reflected measurement luminous beam towards a visualization direction 25.

The second optical means 9 can be such that it permits to obtain an image of the sample surface 21 that is limited by the diffraction limit.

Figure 3:
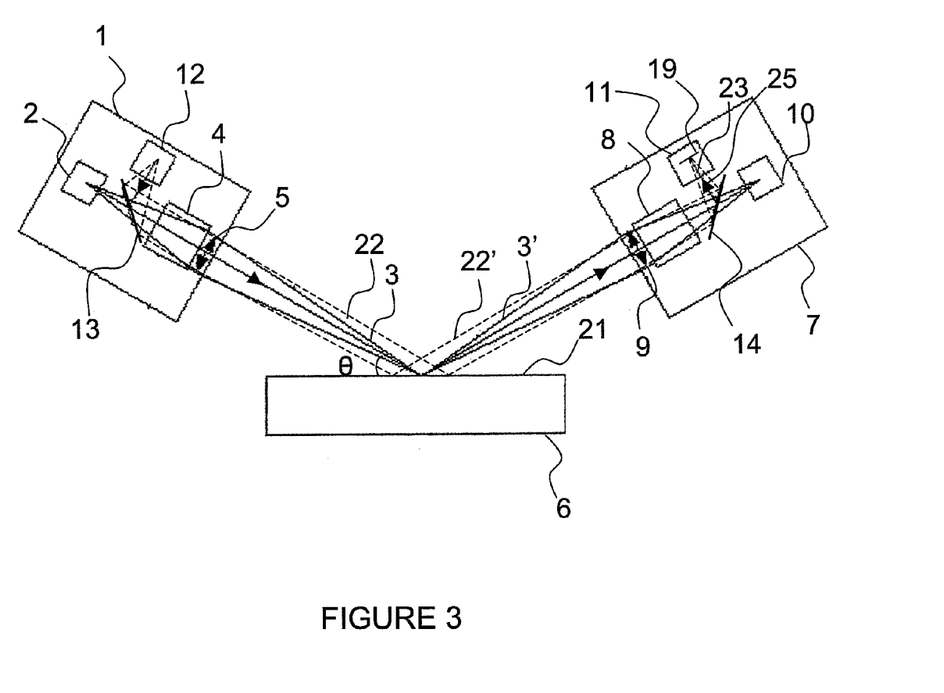
FIG. 3 represents a system for analysing a sample wherein the analyse section comprises an imaging system, according to another embodiment of the invention.

As the part of the reflected visualization luminous beam 23 and the part of the reflected measurement luminous beam are simultaneously transmitted towards the visualization direction 25, the spot of the measurement luminous beam 29 reflected at the sample surface 21 and a part of the sample surface 21 or the whole sample surface 21 are simultaneously visualizable by a user (FIG. 2) or on an imaging system 11 such a CCD detector (FIG. 3).

The system for analysing a sample can comprise optical means such as lens for focusing the part of the reflected visualization luminous beam 23 and the part of the reflected measurement luminous beam on the user eyes or on the imaging system 11.

The lighting of the incident visualization luminous beam 22 should be adjusted in order to avoid the saturation of the imaging system 11 and sufficient to be detected or visualized.

The analyse section 7 can comprise a hole 30 or a transparent porthole between the user eyes and the separation optical means 14. The part of the reflected visualization luminous beam 23 and the part of the reflected measurement luminous beam are transmitted to the user eyes through the hole 30 or the transparent porthole.

The separation optical means 14 can be a beamsplitter or a beam separating cube disposed between the PSA 8 and the detection system 10.

As represented in FIG. 2, the second optical means 9 is disposed between the sample 6 and the PSA 8.

Alternatively the second optical means 9 can be disposed between the PSA 8 and the separation optical means 14.

The optical axis of the reflected visualization luminous beam 22' is identical to the optical axis of the reflected measurement luminous beam 3'. Said optical axis includes the axis between the sample surface 21 and the user eyes or the imaging system 11.

The superposition optical means 13 and the separation optical means 14 enable to integrate the visualization of the spot of the measurement luminous beam 29 and the visualization luminous beam in the optical path of the ellipsometric or polarimetric system.

A large variety of PSG 4 and PSA 8 can be used such those described in the document US2004130717.

In a PSG 4 and a PSA 8, the light polarization can be modulated by a variety of devices such as discrete components inserted and then removed from the light path [Bickel W. S. et al.; Am. J. Phys 53 1984 468], rotating retardation plates [Goldstein D. H.; Appl. Opt. 31 1992 6676], rotating compensators [Collins R. W. and Koh J.; J. Opt. Soc. A 16, 1999 1997], Pockels cells [Delplanecke F.; Appl. Opt. 36 1997 5388 and Compain E. and Drévillon B.; Rev. Sci. Instrum. 68 1997 2671] or photoacoustic modulators [Compain E. and Drévillon B.; Rev. Sci. Instrum. 69, 1998 1574] or photoelastic modulator or Faraday cell.

It is possible to use PSG 4 and PSA 8 including liquid crystal LC variable retarders. Two types of such devices are currently available. First, nematic liquid crystals NLC provide variable retardation with fixed orientation of slow and fast axes, with typical response times of the order of 10 to 100 ms. On the other hand ferroelectric liquid crystals FLC provide fixed retardation, but with slow and fast axis directions which can be electrically switched between two azimuthal angles separated by 45°, in times typically shorter than 100 µs. Such PSG 4 and PSA 8 comprise usually a linear polarizer, a retardation plate, and two liquid crystal modulators. Such PSG 4 can generate up to four independent polarization states.

In this case, after reflection of the incident measurement luminous beam 3 and the incident visualization luminous beam 22 onto the sample 4, each one of the up to four independent polarization states that had been originally generated by the PSG 4, is successively analysed up to four times by the PSA 8, giving as a result 16 independent intensity measurements necessary for the determination of the Mueller-Stokes matrix of the sample 6.

FIG. 3 represents a system for analysing a sample wherein the analyse section 7 comprises an imaging system 11, according to another embodiment of the invention.

The imaging system 11 comprises a detection surface 19. The detection surface 19 detects simultaneously or alternatively the part of the reflected visualization luminous beam 23 and the part of the reflected measurement luminous beam.

After being reflected on the separation optical means 14, the part of the reflected visualization luminous beam 23 and the part of the reflected measurement luminous beam are focused on the detection surface 19.

The detection surface 19 is placed on the image plane of the optical system including the second optical means 9 and the separation optical means 14.

The detection surface 19 can be normal to the visualization direction 25.

The imaging system 11 can be a CCD camera or a hyperspectral detector or the like.

In the case of reflexion measurements, the incident measurement luminous beam 3 and the incident visualization luminous beam 22 are inclined with respect to the sample surface 21.

This inclination leads to an inclination of the image plane which is projected on the detection surface 19. The field of view is thus deformed.

Figure 4:
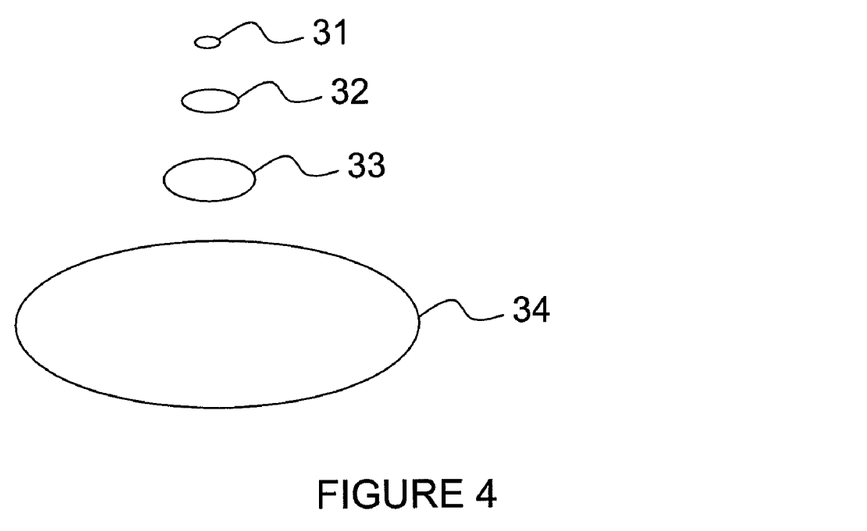
FIG. 4 represents four examples of spots, having different dimension, before the projection of the incident measurement luminous beam on the sample surface.

FIG. 4 represents four examples of spots, having different dimension, before the projection of the incident measurement luminous beam 3 on the sample surface 21.

Figure 5:
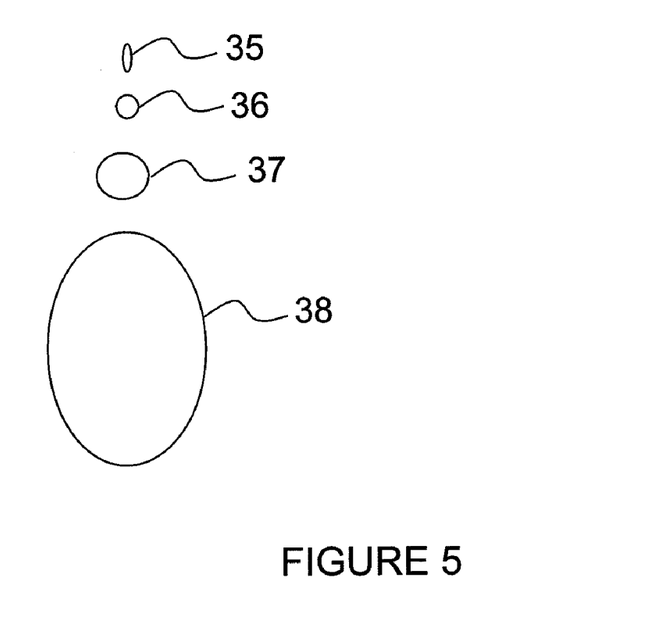
FIG. 5 represents four examples of spots, having different dimension, after the projection of the incident measurement luminous beam on the sample surface according to an incidence angle (90-θ) of 70°.

FIG. 5 represents four examples of spots, having different dimension, after the projection of the incident measurement luminous beam 3 on the sample surface 21 according to an incidence angle ($\theta$) of 70°. FIG. 5 shows that the field of view is deformed.

Before the projection of the incident measurement luminous beam 3 on the sample surface 21, the dimension of the first spot before projection 31 is 10 µm*20 µm in FIG. 4.

After the projection of the incident measurement luminous beam 3 on the sample surface 21 according to the incidence angle ($\theta$) of 70°, the dimension of the first spot after projection 35 is 10 µm*60 µm in FIG. 5.

Before the projection of the incident measurement luminous beam 3 on the sample surface 21, the dimension of the second spot before projection 32 is 60 µm*20 µm in FIG. 4.

After the projection of the incident measurement luminous beam 3 on the sample surface 21 according to the incidence angle ($\theta$) of 70°, the dimension of the second spot after projection 36 is 60 µm in FIG. 5.

Before the projection of the incident measurement luminous beam 3 on the sample surface 21, the dimension of the third spot before projection 33 is 100 µm*33 µm in FIG. 4.

After the projection of the incident measurement luminous beam 3 on the sample surface 21 according to the incidence angle (θ) of 70°, the dimension of the third spot after projection 37 is 100 µm in FIG. 5.

Before the projection of the incident measurement luminous beam 3 on the sample surface 21, the dimension of the fourth spot before projection 34 is 540 µm*250 µm in FIG. 4.

After the projection of the incident measurement luminous beam 3 on the sample surface 21 according to the incidence angle (θ) of 70°, the dimension of the fourth spot after projection 38 is 540 µm*730 µm in FIG. 5.

The first spots 31, 35 have dimensions corresponding to minimal dimensions. The fourt spots 34, 38 have dimensions corresponding to maximal dimensions.

Before the projection of the incident measurement luminous beam 3 on the sample surface 21, the dimension of the field of view is 1.33 mm*1 mm.

After the projection of the incident measurement luminous beam 3 on the sample surface 21 according to the incidence angle (θ) of 70°, the dimension of the field of view on the sample surface 21 is 1.33 mm*3 mm.

For these four examples, the aperture angle is 3.4° in the incidence plane and 6.8° in the plane normal to the incidence plane.

When using a CCD camera as the imaging system 11, the smallest spot of light 35 is detected on three or four pixels.

Figure 6:
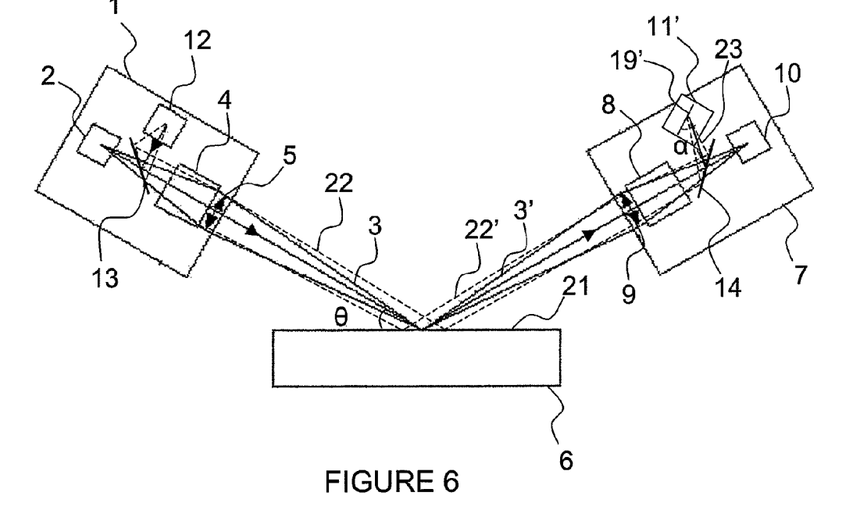
FIG. 6 represents a system for analysing a sample comprising an inclined imaging system according to another embodiment of the invention.

To compensate the inclination of the image plane on which is placed the detection surface 19, the invention provide, in another embodiment, an inclined imaging system 11', represented in FIG. 6. The document DE19707926 discloses an ellipsometer wherein a CCD detector is inclined.

The inclined imaging system 11' has a detection surface 19' which is not normal to the visualization direction 25. The detection surface 19' of the inclined imaging system 11' is inclined with respect to the visualization direction 25 according to an inclination angle (α).

Figure 7:
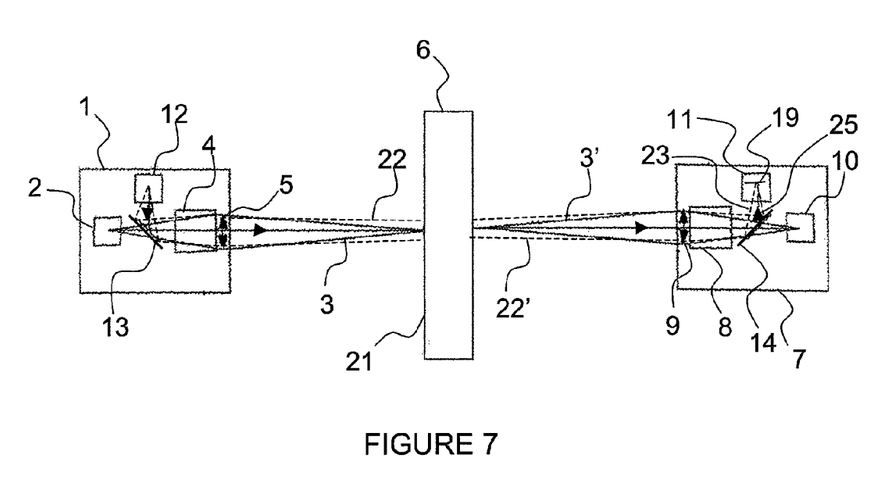
FIG. 7 represents a system for analysing a sample in a transmission configuration.

The system for analysing a sample can be adapted in a transmission configuration, as represented in FIG. 7.

In a transmission configuration, the incident measurement luminous beam 3 and the incident imagery luminous beam 22 projected onto the sample surface 21 can be normal or inclined with respect to the sample surface 21.

While the incident measurement luminous beam 3 and the incident imagery luminous beam 22 projected onto the sample surface 21 are inclined with respect to the sample surface 21, an inclined imaging system 11' is needed to solve the problem of defocalization due to the projection of the incident measurement luminous beam 3 and the incident imagery luminous beam 22 on the sample surface 21.

The first optical means 5 directs the incident measurement luminous beam 3 and the incident visualization luminous beam 22 onto the surface of the sample 21 for generating a transmitted measurement luminous beam 3' and a transmitted visualization luminous beam 22'.

The PSA 8 analyses one or more independent polarization states of the transmitted measurement luminous beam 3' and one or more independent polarization states of the transmitted visualization luminous beam 22'. The second optical means 9 focuses the transmitted measurement luminous beam 3' onto the detection system 10 which measures intensity of the transmitted measurement luminous beam 3' as a function of polarization states.

The separation optical means 14 transmits a part of the transmitted visualization luminous beam 23 and a part of the transmitted imagery luminous beam 22' towards the visualization direction 25.

The system for analysing a sample 6 can be a monochromatic ellipsometer wherein the light source 2 is a single wavelength laser or diode laser.

It can be a spectroscopic ellipsometer wherein the light source is a multicoloured light-emitting diode or a large spectral band light source and the detection system 10 comprises a monochromator or a spectrograph.

It can be a polarimeter or a dichrograph.

When using an adapted illumination source 12 such as a xenon source and an adapted imaging system 11 such as a CCD detector or a hyperspectral detector, it is possible to realise an ellipsometric or polarimetric image of the sample surface 21.

The document U.S. Pat. No. 6,798,511 discloses an imaging ellipsometer using a CCD detector as an imaging system 11. The document WO 2005083352 discloses an imaging ellipsometer using a hyperspectral detector as an imaging system 11.

The group composed of the light source 2, the polarisation state generator PSG 4, the first optical means 5, the second optical means 9, the polarisation state analyser PSA 8 and the detection system 10 forms a "spectroscopic ellipsometer".

And the group composed of the illumination source 12, the polarisation state generator PSG 4, the first optical means 5, the second optical means 9, the polarisation state analyser PSA 8 and the imaging system 11 forms an "imaging ellipsometer".

The step of visualization of an area localized around the measurement point on the sample surface 21 consists of an acquisition of an ellipsometric image of this area on the sample surface 21.

The superposition optical means 13 enabling to send the incident visualization luminous beam 22 onto the surface of the sample 21 and the separation optical means 14 enabling to transmit a part of the reflected or transmitted visualization luminous beam 23 towards a visualization direction 25 permit to realise a coupling between said "spectroscopic ellipsometer" and said "imaging ellipsometer".

A measurement with the "spectroscopic ellipsometer" can be done on a limited area of the sample surface 21. This measurement is a polychromatic measurement which supplies several informations concerning the limited area of the sample surface 21 such as the dispersion law of a layer of the sample 6.

Using the dispersion law of the layer, the imaging ellipsometer enable to measure the uniformity of the layer. It is possible to obtain a monochromic ellipsometric image of the layer of the sample 6 in a plane which is parallel to the sample surface 21.

As the imaging system 11 is a hyperspectral detector, the hyperspectral detector receives a part of the reflected or transmitted visualization luminous beam 23 to produce a spectroscopic image of one sample layer.

The illumination source 12 lights an enlarged area of the sample surface 21 or the whole sample surface 21. The imaging system 11 detects the enlarged area of the sample surface 21 or the whole sample surface 21.

All the pixels of the imaging system 11 are simultaneously polarized which leads to reduce the measurement time.

Each pixel of the imaging system 11 can generate an ellipsometric measurement corresponding to the image pixel in the incident visualization beam 40 on the sample surface. The imaging ellipsometer measurement can be performed at a single wavelength, either using a single wavelength visualization light source such as a diode laser, either by placing an interference filter in front of the imaging system 11. It is thus possible to generate an ellipsometric image of the sample at that wavelength. Simultaneously or successively, the system can perform an ellipsometric imaging and provides visual information about sample surface layer non uniformity for example.

It should be noted that a single instrument provides coupled spectroscopic ellipsometric measurement of a spot precisely positioned on the sample surface and ellipsometric imaging of an area localized around the spectroscopic ellipsometer beam spot. These two measurements are obtained without moving the sample, and without moving the ellipsometer system components. The spectroscopic ellipsometry measurement and the ellipsometric imaging measurement provide complementary informations, that can be combined, or cross-correlated for further sample analysis.

The measurements with the "spectroscopic ellipsometer" and the "imaging ellipsometer" can be done simultaneously in order to reduce the measurement time or alternatively.

In order to realise the measurements alternatively, the superposition optical means 13 and/or the separation optical means 14 can be rotary mirrors.

The invention claimed is:

1. A system for analyzing a sample having at least a sample surface, the system comprising:
    a light source that emits an incident measurement luminous beam;
    an illumination source that emits an incident visualization luminous beam;
    superposition optics positioned to combine and redirect the incident measurement luminous beam and the incident visualization luminous beam along a common optic axis through a polarization state generator and toward the sample surface to form a measurement luminous beam spot and an enlarged visualization luminous beam spot on the sample surface; and
    separation optics that direct a first portion of the visualization luminous beam and a first portion of the measurement luminous beam reflected or transmitted by the sample surface toward a visualization direction to permit a user to view an image of the visualization beam spot and the measurement beam spot.

2. The system of claim 1 further comprising:
    an imaging system having a detection surface positioned to receive the first portion of the visualization luminous beam and the first portion of the measurement luminous beam from the separation optics.

3. The system of claim 2 wherein the detection surface is inclined with respect to the visualization direction by an inclination angle alpha.

4. The system of claim 1 wherein the light source comprises a wide spectral band light source.

5. The system of claim 1 wherein the light source comprises a multi-colored light emitting diode.

6. The system of claim 1 further comprising:
    a detection system having a monochromator or a spectrograph for receiving a second portion of the visualization measurement beam from the separation optics to analyze the measurement spot on the sample surface.

7. The system of claim 1 wherein the superposition optics and the separation optics comprise rotating mirrors.

8. The system of claim 7 wherein the rotating mirrors of the superposition optics are synchronized with the rotating mirrors of the separation optics to provide successive spectroscopic measurement of the measurement beam spot and imaging of the visualization beam spot.

9. The system of claim 1 wherein the superposition optics and the separation optics each comprises one of a beam splitter and a beam separating cube.

10. The system of claim 9 wherein the superposition optics and the separation optics are synchronized to provide simultaneous spectroscopic measurement of the measurement beam spot and imaging detection of the visualization beam spot.

11. The system of claim 1 wherein the light source and the illumination source comprise light-emitting diodes and wherein the polarization state generator comprises a liquid crystal variable retarder, the system further comprising:
    a polarization state analyzer positioned to receive at least the incident measurement luminous beam transmitted or reflected from the sample surface.

12. The system of claim 11 wherein the polarization state analyzer comprises a liquid crystal variable retarder.

13. The system of claim 11 further comprising an optical element for focusing light from the separation optics onto a detection system, wherein the optical element is disposed between the sample and the polarization state analyzer.

14. The system of claim 1 further comprising an optical element for focusing the incident measurement luminous beam on the sample surface, the first optical element disposed between the light source and the polarization state generator.

15. The system of claim 1 further comprising:
    a hyperspectral detector positioned to receive the first portion of the visualization luminous beam from the separation optics to produce a spectroscopic image of one layer of the sample.

16. A method for analysing a sample, the method comprising:
    illuminating the sample with a measurement beam and a coaxially propagating visualization beam;
    performing an ellipsometric measurement using a portion of the measurement beam reflected or transmitted by the sample, wherein performing an ellipsometric measurement comprises: producing one or more polarization states of the measurement beam; focusing the measurement beam onto the sample; analyzing one or more polarization states of the measurement beam reflected or transmitted by the sample; and measuring intensity of the reflected or transmitted measurement beam as a function of polarization states; and
    imaging the visualization beam, wherein imaging comprises: directing a first portion of the measurement beam and the visualization beam reflected or transmitted by the sample in a visualization direction; and
    directing a second portion of the measurement beam and the visualization beam reflected or transmitted by the sample to a detector for performing the ellipsometric measurement.

17. The method of claim 16 wherein illuminating the sample comprises:
    combining the measurement beam and the visualization beam;
    focusing the measurement beam on a surface of the sample to form a measurement beam spot; and
    steering the visualization beam to illuminate an area localized around the measurement beam spot on the sample surface.

18. The method of claim 16 wherein illuminating the sample comprises:
    successively illuminating the sample with the measurement beam and the visualization beam.

19. A system for analyzing a sample, the system comprising:
- a light source that emits an incident measurement luminous beam;
- a polarization state generator that produces one or more independent polarization states of the incident measurement luminous beam;
- an optical element that focuses the incident measurement luminous beam onto the sample;
- an illumination source that emits an incident visualization luminous beam;
- superposition optics that combine the measurement and visualization beams along a common optical axis;
- a polarization state analyzer that analyzes one or more independent polarization states of the measurement luminous beam reflected or transmitted by the sample;
- a detection system that measures intensity of the measurement luminous beam reflected or transmitted by the sample as a function of the polarization states determined by the polarization state analyzer; and
- separation optics that direct a first portion of the measurement luminous beam and the visualization luminous beam in a visualization direction and a second portion of the measurement luminous beam and the visualization luminous beam to the detection system.

20. The system of claim 19 wherein the separation optics and the superposition optics each comprise a rotating mirror.

21. The system of claim 20 wherein the rotating mirror of the superposition optics is synchronized with the rotating mirror of the separation optics to successively reflect the measurement luminous beam and the visualization luminous beam.

* * * * *